(12) United States Patent
Chadwick et al.

(10) Patent No.: US 9,810,678 B2
(45) Date of Patent: Nov. 7, 2017

(54) DRIFTING EXPOSURE SYSTEM FOR SAMPLING STORMWATER DISCHARGE PLUMES

(71) Applicants: David Bartholomew Chadwick, San Diego, CA (US); Jonathon Keith Oiler, San Diego, CA (US); Matthew Joseph Nicholson, San Diego, CA (US)

(72) Inventors: David Bartholomew Chadwick, San Diego, CA (US); Jonathon Keith Oiler, San Diego, CA (US); Matthew Joseph Nicholson, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 95 days.

(21) Appl. No.: 14/616,988

(22) Filed: Feb. 9, 2015

(65) Prior Publication Data

US 2016/0231302 A1    Aug. 11, 2016

(51) Int. Cl.
G01N 1/12         (2006.01)
G01N 33/18        (2006.01)
G01N 1/20         (2006.01)

(52) U.S. Cl.
CPC .......... *G01N 33/1886* (2013.01); *G01N 1/12* (2013.01); *G01N 1/20* (2013.01)

(58) Field of Classification Search
CPC ...... G01N 1/20; G01N 33/1886; G01N 11/00; G01N 1/12; G06F 17/5009
USPC ............................................... 73/864, 864.51
See application file for complete search history.

(56) References Cited

U.S. PATENT DOCUMENTS

| 4,004,265 A * | 1/1977 | Woodruff ............. | G10K 11/008 367/130 |
| 7,591,979 B2 * | 9/2009 | Hill .......................... | G01N 1/14 422/62 |
| 9,404,906 B2 * | 8/2016 | Thomas ................. | G01C 13/00 |

(Continued)

OTHER PUBLICATIONS

K.W. Lee, D.-H. Lee, U.-S. Jeong, J.Y. Yang, H.K. Jun, J.H. Park, "Implementation of embedded system for autonomous buoy," IEEE Oceans, pp. 1-4, 2011.

*Primary Examiner* — Helen Kwok
*Assistant Examiner* — Nashmiya Fayyaz
(74) *Attorney, Agent, or Firm* — SPAWAR Systems Center Pacific; Kyle Eppele; J. Eric Anderson

(57) ABSTRACT

A drifting buoy sampler system for a stormwater discharge plume formed from stormwater discharged into coastal waters. The system compresan electronics sampling pod for collecting integrated water samples within the stormwater plume as the buoy system drifts with the stormwater plume near the water surface as the plume travels out to sea. The pod includes a watertight section including a GPS/radio module for providing GPS (geo-position) location information and a processor for monitoring and controlling the sampling rate, a pump module and a battery module; a passive sampler bag for collecting the integrated water samples; a free flooding section including a composite sample bag module such that the pump module pumps collected samples from the passive sampler bag to the composite sample bag module at a predetermined sampling rate and a ballast module for providing ballast to the system when drifting within the plume.

5 Claims, 5 Drawing Sheets

(56) References Cited

U.S. PATENT DOCUMENTS

| | | | |
|---|---|---|---|
| 2012/0222500 A1* | 9/2012 | Riess | G01N 1/02 73/863.23 |
| 2014/0216325 A1* | 8/2014 | Hardy | B63G 8/001 114/321 |
| 2016/0018377 A1* | 1/2016 | Corbett | G01N 33/1886 414/137.9 |

* cited by examiner

DRIFTING EXPOSURE SYSTEM FOR SAMPLING STORMWATER DISCHARGE PLUMES

FEDERALLY-SPONSORED RESEARCH AND DEVELOPMENT

This invention (Navy Case No. 103,249) is assigned to the United States Government and is available for licensing for commercial purposes. Licensing and technical inquiries may be directed to the Office of Research and Technical Applications, Space and Naval Warfare Systems Center, Pacific, Code 72120, San Diego, Calif., 92152; voice (619) 553-2778; email T2@spawar.navy.mil.

BACKGROUND

After rain events, the water discharged into coastal waters is known as stormwater. Stormwater discharges (an example is shown in FIG. 1), can carry with them a host of pollutants in the form of contaminated sediment. These events span coastal sites, including nearly every DoD coastal site, and are linked to all aspects of regulatory compliance including pollution discharge permitting, source control strategies, and environmental restoration programs which cost the Navy hundreds of millions of dollars annually.

The fact that these events do not occur as point sources make them extremely difficult to characterize and control. Sediment transport models often do not have enough resolution to resolve stormwater discharges and current field-based sampling strategies such as sampling near the outfalls only provides indirect evidence as to the transport, impact, and the ultimate fate of the contaminated sediment in the coastal waters.

SUMMARY

A drifting buoy sampler system, also referred to as the buoy system, and the sampler herein, for a stormwater discharge plume formed from stormwater discharged into coastal waters. The system comprises an electronics sampling pod for collecting integrated water samples within the stormwater plume as the buoy system drifts with the stormwater plume near the water surface as the plume travels out to sea. The pod includes a watertight section including a GPS/radio module for providing GPS (geo-position) location information and a processor for monitoring and controlling the sampling rate, a pump module and a battery module; a passive sampler bag for collecting the integrated water samples; a free flooding section including a composite sample bag module such that the pump module pumps collected samples from the passive sampler bag to the composite sample bag module at a predetermined sampling rate and a ballast module for providing ballast to the system when drifting within the plume.

BRIEF DESCRIPTION OF THE DRAWINGS

Throughout the several views, like elements are referenced using like references, wherein.

DETAILED DESCRIPTION OF THE EMBODIMENTS

Figure 1:
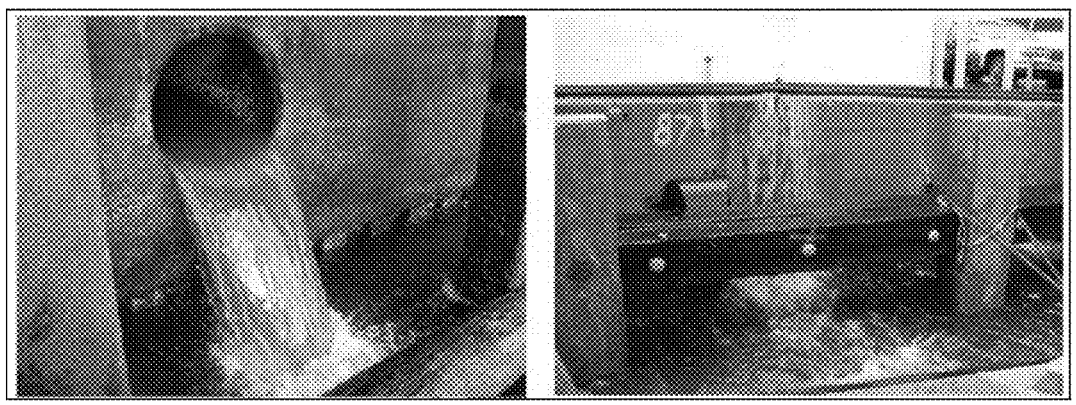
FIG. 1 shows storm drain and sheet flow discharges at Naval Base San Diego.
Figure 2:
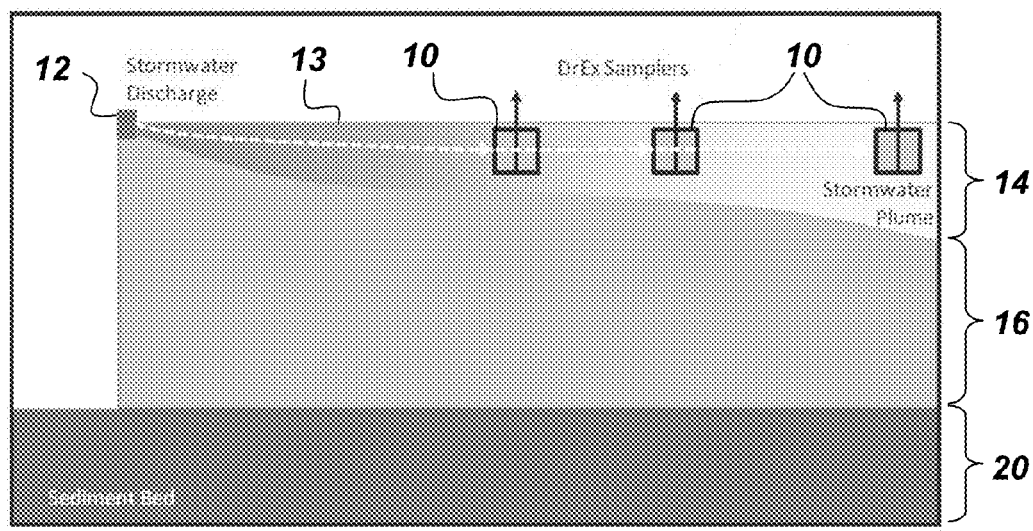
FIG. 2 shows a view of a drifting buoy sampler system.
Figure 3:
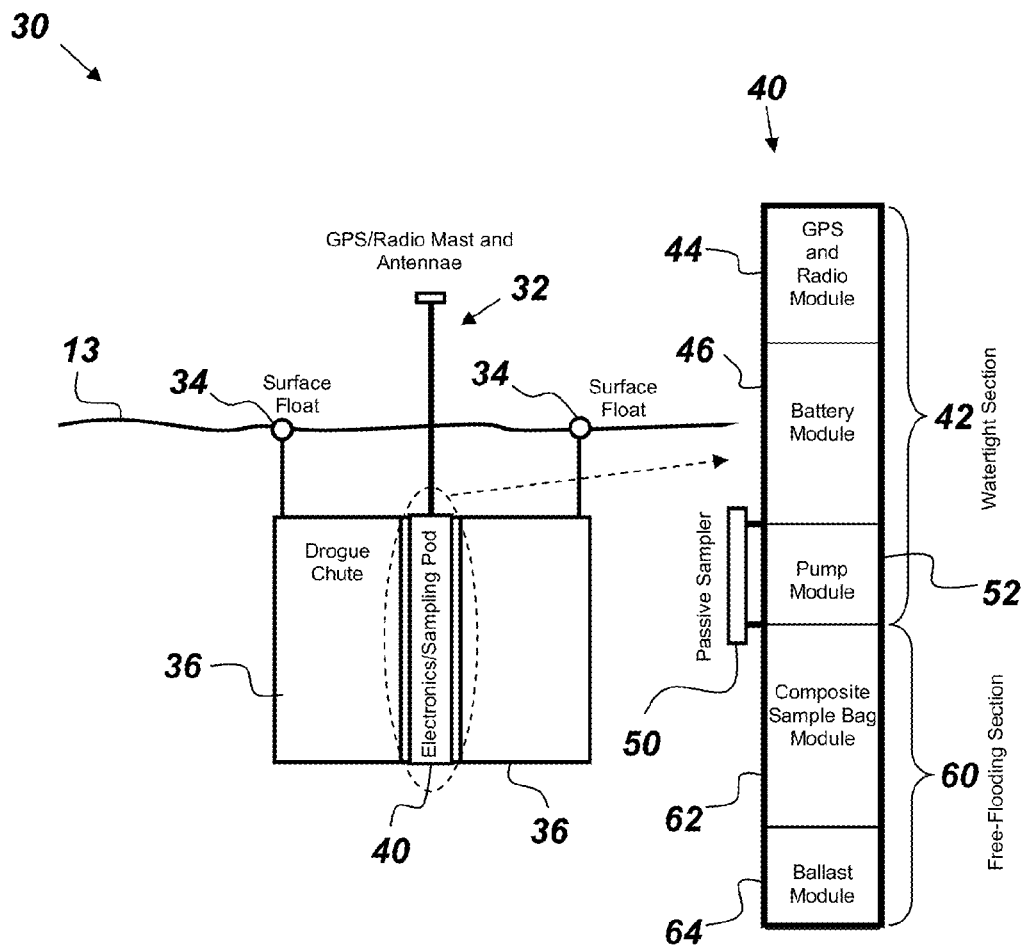
FIG. 3 is a schematic diagram showing an embodiment of a drifting buoy sampler system designed for integrated and passive sampling of a stormwater plume.

Referring to FIGS. 2-3, one embodiment provides a capability to do both composite and passive sampling of the stormwater discharge plume as the plume moves from the source 12 and disperses out in the coastal waters.

The buoy system collects integrated water samples within stormwater discharge plumes in coastal waters as the samples travel away from the source. The system provides the capability to pump seawater collected from the stormwater plume through a passive sampler, such as diffusive gradients in thin films or diffusive equilibrium in thin films and/or into a composite sampler for later laboratory measurements related to the identification and concentration of organic and metal contaminants after the buoy is retrieved.

The buoy system can be equipped with GPS so that the geo-position can be correlated with the types of time-weighted concentration of contaminants from specific sources. The buoy system can also be equipped with communications to monitor and control the sampling.

The drifting buoy sampler system drifts with the stormwater plume which stays near the surface as it travels out to sea, as shown in FIG. 2.

One embodiment includes a GPS/communications unit, a pump and composite sampling bag, and a battery and microcontroller for setting the sampling rate. The battery and pump are not exposed to the seawater, while the composite sampling bag can be in a free-flooded chamber (see FIG. 3).

FIG. 3 is a schematic diagram showing the key module designed for integrated and passive sampling of the stormwater plume.

During this time, the buoy system collects composite and passive samples of the seawater and its contents. While collecting an integrated sample, the GPS position of the buoy will be recorded. The combined data provides insight into how specific contaminants disperse from the plume as they are dispersed out into the seawater.

Referring to FIG. 2, the drifting buoy sampler system 10 drifts with a stormwater plume 14. The plume 14 is shown above the sea water 16 and sediment bed 20 in FIG. 2. In the embodiment of the buoy system, 10 shown in FIG. 2, the buoy system 10 stays near the surface 13 as the buoy system 10 travels out to sea, along with the stormwater plume 14.

FIG. 3 shows a schematic diagram of an embodiment 30 of the drifting buoy sampler system 10 designed for integrated and passive sampling of a stormwater plume. The embodiment 30 includes a GPS/radio mast and antenna 32, surface floats 34, drogue chute 36, and electronics/sampling pod 40.

The pod 40, shown in more expanded form in the right side of FIG. 3, includes a watertight section 42, including GPS/radio module 44, battery module 46, passive sampler 50, and pump module 52.

The pod 40 also includes a free flooding section 60, which includes composite sample bag module 62 and ballast module 64.

The embodiment 30 of the drifting buoy sampler system 10 collects an integrated sample of seawater content during the entire period the plume travels out to sea, not just at the source of the plume where the contaminants will be strongest. The embodiment 30 of the drifting buoy sampler system 10 comprises integrating a composite and passive sampling mechanism with the drifting buoy sampler system 10. Because the drifting buoy sampler system 10 automatically follows the plume, the entire sampling event can be done autonomously with no operator intervention except to deploy and retrieve the system.

The embodiment 30 of the drifting buoy sampler system 10 allows for linking the sampling time to exposure durations for organisms. For example many toxicity tests are associated with 48-96 hour exposure times. Thus a composite sample collected over that time period would provide a realistic estimate of the concentration that an organism (like a planktonic larvae) that was drifting with the plume would be exposed to.

Many samplers can be released in groups or over time to provide more detailed descriptions and statistical information about the dispersion, concentrations and exposure levels in these plumes. An interface of the sampler and sensors to the user via satellite, cell phone, radio, Bluetooth or WiFi will allow for both monitoring of the sampling process and control of the sampler remotely.

Alternatively, one could bring along multiple composite sampling bags and fill the bags at different periods of time as the buoy drifts away from the source, thereby giving an indication of how the concentrations of contaminants change with distance from the source. The sampling could also be linked to the feedback from various sensors. For instance with feedback from the GPS it could be constrained to sampling in certain spatial areas. With feedback from a salinity sensor, it could be constrained to only sampling while it was in the freshwater storm plume. With feedback from a turbidity sensor it could be linked to sampling when the particle concentrations were in a certain range. The composite sampler could also be replaced by a sorption type column sampler filled with reactive material so that it pre-concentrated certain contaminants of interest.

The drifting buoy sampler system 10 could also utilize passive samplers such as Polyethylene Sampling Devices that can simply be attached to the drifting buoy sampler system 10 and equilibrate with the water contaminants over time.

Figure 4:
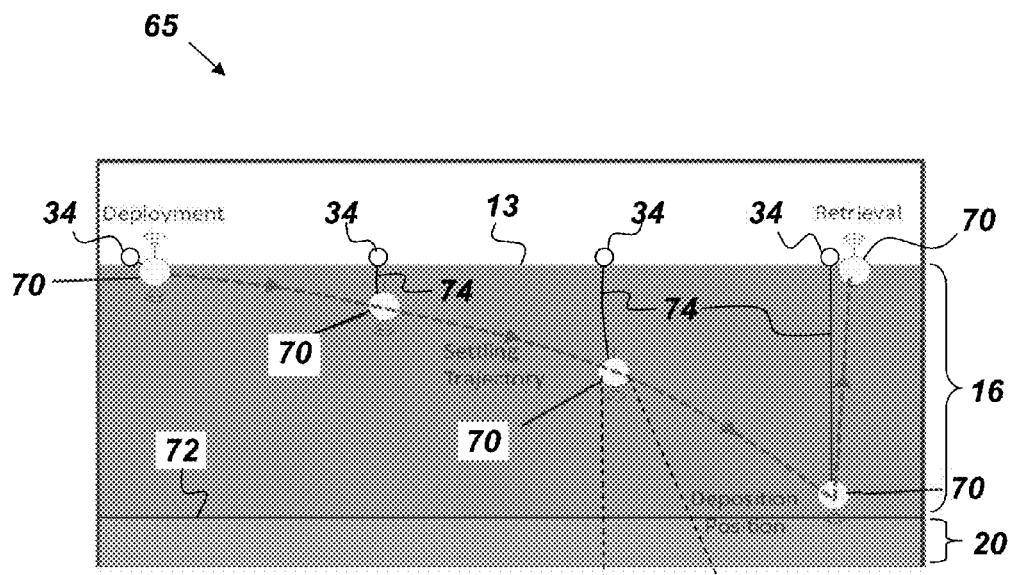
FIG. 4 is a schematic showing how a drogue chute and winch system mimics the settling trajectory of a particle-of-interest.
Figure 4:
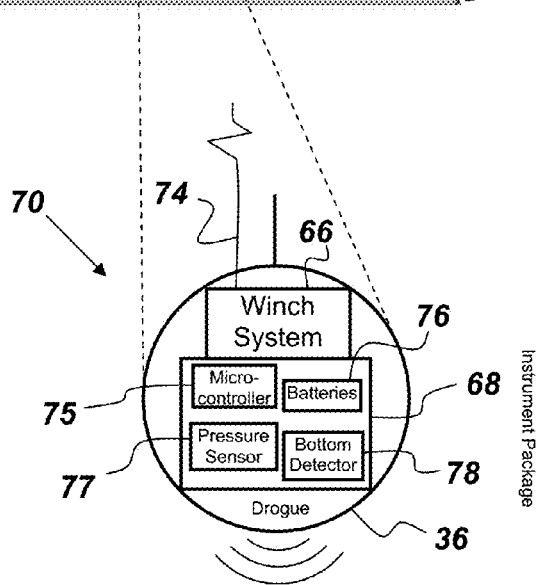
Figure 5:
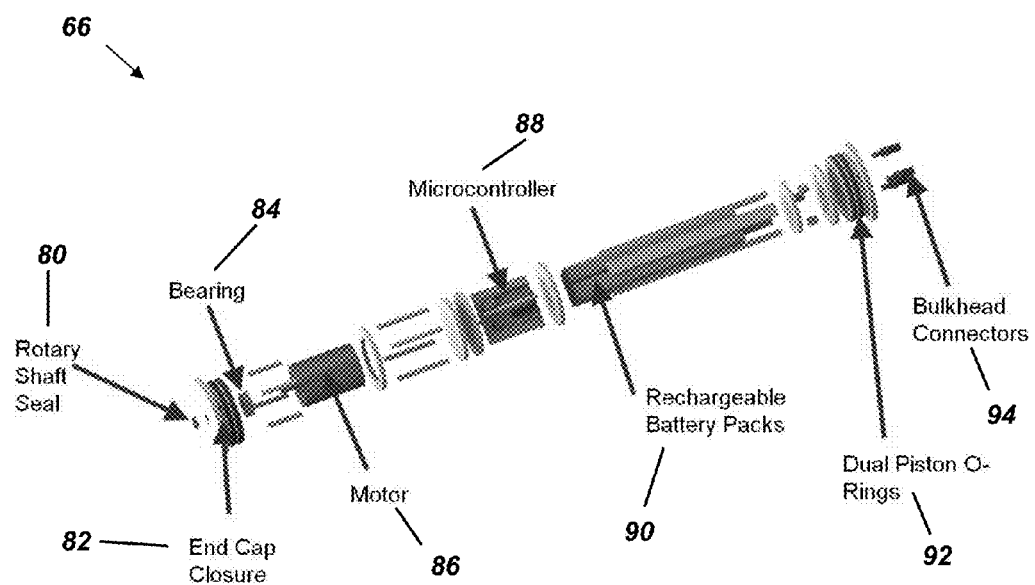
FIG. 5 is a CAD drawing showing the winch system which lowers itself and the drogue chute to the bottom of the seafloor.

Referring now to FIGS. 4-5, one an embodiment 65 of the drifting buoy sampler system 10 can mimic the transport and deposition of specific sizes of contaminated sediment particles as they travel from the source and eventually settle on the seafloor 72. A controllable-descent rate underwater winch system 66 lowers an instrument package 68 and drogue 36 to the seafloor 72. The combination of the winch system 66, instrument package 68, and drogue 36 is represented in FIG. 4 by reference character 70. In addition, the embodiment 65 of the drifting buoy sampler system 10 is equipped with communications to monitor and control the descent rate and detect when it reaches the seafloor 72.

The embodiment 65 of the drifting buoy sampler system 10 uses GPS which tracks the location of the surface float 34 at the surface 13 of the water. Underneath the surface float 34 is a drogue/winch system/instrument package 70 which can be lowered to the seafloor 72 at a controlled descent rate (e.g., between 0.1-10 mm/s)—a range that covers a wide swath of various size sediment particles.

Lowering the drogue/winch system/instrument package 70 ensures that the drifting buoy sampler system 10 drifts laterally with the underwater current at the same velocity as the particles of interest (FIG. 4). The speed at which the drogue/winch system/instrument package 70 is lowered can be controlled to mimic the settling rate of the sediment particle of a particular size with use of a pressure sensor. FIG. 4 shows the settling of the drogue/winch system/ instrument package 70 from deployment in a settling trajectory to the deposition position, and finally at the retrieval of the drogue/winch system/instrument package 70.

By using bottom-detection sensors, we can pinpoint precisely the GPS location where the controlled-descent drogue/winch/instrument package 70 reaches the seafloor 72. Using embodiment 65 of the drifting buoy sampler system 10, we can determine the depositional footprint of contamination on the seafloor 72 to target for future analysis (impact and fate) and potential cleanup.

FIG. 5 is an expanded view drawing of components of the winch system 66. The winch system 66 was designed as a motor-controlled winch mounted within the drogue 36 (to minimize drag effects) that releases a slack line 74 (such as a fishing wire) to provide slack to the negatively buoyant drogue chute 36 and winch system 66. The winch system 66 is mounted on an instrument package 68 that contains a microcontroller 75, batteries 76, along with a pressure sensor 77 and bottom detection sensor 78 to carefully control the descent rate and mark the time when the system reaches the seafloor. This time is matched to the GPS-time monitored at the surface float 34 and the coordinates are used to mark the location where the contaminated particles have likely been deposited.

FIG. 5 is a CAD drawing showing the winch system 66 which lowers itself and the drogue chute 36 to the bottom of the seafloor 72. The winch system 66 in FIG. 5 includes rotary shaft seal 80; end cap closure 82; bearing 84; motor 86; microcontroller 88; rechargeable battery packs 90; dual piston O-rings 92; and bulkhead connectors 94. Depth and bottom detection sensors (not shown in FIG. 5) can be attached to the winch system 66.

This system tracks the three-dimensional trajectories of sediment originating from a stormwater discharge plume to its final depositional location on the seafloor 72. The winch system 66 and instrument package 68 can be mounted within the drogue 36. The drogue/winch system/instrument package 70 can be lowered to the seafloor 72 at a controllable descent rate without operator intervention. The locations where the particles are deposited provide the capability of future sediment-contaminant analyses of these areas which can provide more information about whether a clean-up is necessary. In addition, any potential cleanups might have lower costs associated with a better understanding of the contaminant footprint and more success by cleaning only areas that require it.

Buoyancy engines could be one possible alternative to lowering the drogue 36 and instrument package 68 with the underwater winch system 66. However, controlling the very slow descent rate could be difficult. In addition, the buoyancy engine would need to resurface to determine its location and the lag-time associated with resurfacing and re-acquiring GPS could negate this systems usefulness.

A composite or passive water sampling system could provide the capability to sample the sediment as it traverses the water column to determine how the contaminant species change with distance and depth from the source. Additional turbidity sensors could be used to measure how particles concentrations change as a function of distance and depth.

From the above description, it is apparent that various techniques may be used for implementing the concepts of the present invention without departing from its scope. The described embodiments are to be considered in all respects as illustrative and not restrictive. It should also be understood that system is not limited to the particular embodiments described herein, but is capable of many embodiments without departing from the scope of the claims.

What is claimed is:

1. A drifting buoy sampler system for a stormwater discharge plume formed from stormwater discharged into coastal waters, the system comprising:
    a surface float;
    a winch system operatively coupled to the surface float via a slack line;
    a drogue chute connected to the winch system;
    an instrument package, wherein the winch system is mounted on the instrument package, and wherein the instrument package is configured to control a descent rate of the winch system, the drogue chute, and the instrument package toward a seafloor along a trajectory that mimics a sediment particle of a desired size; and
    wherein the instrument package comprises a microcontroller operatively coupled to the winch system, a pressure sensor configured to output pressure data to the microcontroller, and a bottom detection sensor communicatively coupled to the microcontroller, wherein the microcontroller is configured to control the descent rate of the winch system, the drogue chute, and the instrument package based on the pressure data and to record the time at which the winch system, the drogue chute, and the instrument package reach the seafloor.

2. The drifting buoy sampler system of claim 1, further comprising a sampling pod connected to the surface float for collecting integrated water samples within the stormwater plume as the drifting buoy sampler system drifts with the stormwater plume near the water surface as the plume travels out to sea, wherein the sampling pod comprises:
    a GPS/radio module configured to provide GPS (geoposition) location information;
    a processor communicatively coupled to the GPS/radio module and configured to monitor and control collection of water samples at a sampling rate;
    a passive sampler communicatively coupled to the processor;
    a composite sample bag module; and
    a pump module configured to pump water from near the water surface through the passive sampler and into to the composite sample bag module at the predetermined sampling rate.

3. The drifting buoy sampler system of claim 2, wherein the passive sampler, the composite sample bag module, and the pump are located in a free flooding section of the sampling pod.

4. The drifting buoy sampler system of claim 3, wherein the sampling pod further comprises a ballast module for providing ballast to the system when drifting within the plume.

5. The drifting buoy sampler system of claim 4, wherein the processor is configured to record time and surface buoy GPS position data for each collected sample so as to provide contaminate dispersal information from the plume.

* * * * *